United States Patent [19]

Couvillion

[11] Patent Number: 4,958,527

[45] Date of Patent: Sep. 25, 1990

[54] SAMPLE VALVE ASSEMBLY FOR ON-LINE SAMPLING OF GRANULAR MATERIALS

[75] Inventor: Mark C. Couvillion, Mt. Clemens, Mich.

[73] Assignee: The Dow Chemical Company, Midland, Mich.

[21] Appl. No.: 366,815

[22] Filed: Jun. 14, 1989

[51] Int. Cl.$^5$ .......................... G01N 1/08; G01N 1/14
[52] U.S. Cl. .................. 73/863.86; 73/863.83; 73/864.43
[58] Field of Search ........... 73/863.86, 864.43, 863.83, 73/863.84

[56] References Cited

U.S. PATENT DOCUMENTS

| | | | |
|---|---|---|---|
| 3,561,274 | 2/1971 | Haunschild | 73/863.86 |
| 3,786,682 | 1/1974 | Winter et al. | 73/863.86 |
| 3,804,365 | 4/1974 | Fetterolf et al. | 251/189 X |
| 3,847,023 | 11/1974 | Mallander et al. | 73/864.43 |
| 4,454,943 | 6/1984 | Moller | 73/863.86 X |
| 4,483,206 | 11/1984 | Thompson | 73/863.85 |
| 4,594,903 | 6/1986 | Johnson | 73/863.86 |
| 4,594,904 | 6/1986 | Richter | 73/863.86 |
| 4,854,189 | 8/1989 | Mauleon et al. | 73/863.86 |

OTHER PUBLICATIONS

"Strahman Sampling Valve", 2 page brochure.

Primary Examiner—Tom Noland

[57] ABSTRACT

A valve assembly for on-line removal of representative granular material such as catalyst samples from a process vessel such as a reactor including a plunger type valve having an extension tube of catalyst-compatible material attached to the sampling end of the valve through which sample can be extracted from a predetermined location in the catalyst bed via a flexible auger, or sucked by vacuum into a collection pot, under an inert atmosphere; and the sampling process using the valve assembly. The valve assembly and process allows sampling without contaminating or modifying the oxidation state of the sample or damaging the catalyst, reduces reactor downtime, and allows repeated sampling without the problem of leakage.

10 Claims, 2 Drawing Sheets

SAMPLE VALVE ASSEMBLY FOR ON-LINE SAMPLING OF GRANULAR MATERIALS

BACKGROUND OF THE INVENTION

This invention relates to a sample valve assembly and process for sampling a solid granular material from a container or vessel. The sample valve and process of present invention advantageously may be used for removing a catalyst sample from a process vessel such as a reactor vessel.

Effective representative sampling, for example, of catalyst beds in commercial reactors, is necessary to determine the effects of various process conditions on ultimate catalyst performance. Effects of feed poisons, temperature profile, sintering, flow distribution, attrition, crush strength, and packing height, in addition to other parameters, need to be known about individual beds of catalyst in process reactors as a means of improving performance, minimizing downtime, identifying poisons, and monitoring physical properties.

Present sampling techniques have the disadvantages of: (1) contaminating the sample: (2) changing the oxidation state of the sample: (3) changing the physical properties of the catalyst:(4) affecting the flow distribution characteristics of the reactor: (5) requiring significant downtime: and (6) potentially affecting the integrity of the reactor, such as, for example, pulling out a thermowell, taking a sample, and not being able to replace the thermowell and/or get a leak-tight seal.

Proper sampling of a catalyst is necessary to be able to gather the most usable information from a sample or series of samples. Analytical techniques are available that enable detailed analysis of catalyst morphology to the molecular level, but there is no adequate technique to enable true, unadulterated sampling of catalyst from commercial reactors. Samples taken by present methods are questionable at best and useless or damaging to the system at worst.

Some prior art catalysts, for example, Dow Type KLP catalyst commercially available from The Dow Chemical Company, in its active form is in the reduced state and is very sensitive to oxygen. In a commercial reactor in the reduced state, the catalyst may also have some hydrocarbon absorbed to its surface. The hydrocarbon, combined with its sensitivity to oxygen, makes the catalyst potentially pyrophoric if sampled in its active form. The catalyst is also sensitive to other process parameters that may affect crush strength and/or pellet integrity due to location in the reactor. Existing means of sampling, as described below, are inadequate to get a true representative sample of the catalyst.

Present art methods for sampling a catalyst such as Dow Type KLP catalyst in a commercial reactor include: (1) using a grain probe which may/can be compartmentalized and pushed through the catalyst bed of the reactor with an auger, if not just pushed into the catalyst bed by force: (2) removing an upper manway, piping connection, or thermowell of the reactor and collecting a sample: or (3) emptying the reactor and catching samples as the catalyst comes out. Each of these methods has severe limitations to enabling the taking of a true representative sample.

All of the above techniques require opening the reactor in one form or fashion, effectively exposing the catalyst to the atmosphere and, if the reactor is not adequately purged or otherwise cleared, exposing the sampling personnel to the previous contents of the reactor Probes, whether forced into the catalyst bed or "screwed" as with an auger, potentially cause damage to catalyst samples, especially the more dense packing, pelletized and/or extruded varieties of catalyst, the extent of the damage of which is not known. Forcing a probe into a catalyst bed causes attrition or crushing of the sample, resulting in obtaining a sample that is not representative of the true physical state of the catalyst in the reactor. Removal of manways, piping, or thermowells involves affecting the integrity of the reactor vessel itself, and also necessitates the vessel being reasonably cooled to allow work on the vessel.

A principal drawback of the prior art methods, in addition to being slow and labor intensive, is that samples are typically taken only from the outer perimeter of the catalyst bed, unless probe devices are used, in which case the sample suffers potential physical degradation. The above prior art methods, for the purpose of safety to sampling personnel, necessitate that the catalyst to be sampled be in some non-reactive form, such that as the vessel is opened, and a sample is taken, the catalyst does not react with the atmosphere or affect the sampling personnel in any way. In the case of dropping the catalyst charge, and sampling as the material is removed from the reactor, the relative position of the sample in the bed is estimated at best, and may be a blend of catalyst from different areas of the reactor.

It is desired to provide a sample valve and process particularly useful for allowing an operator to remove a catalyst sample from a process vessel (1) without changing the oxidation state of the catalyst sample, e.g. for catalysts that are air or moisture sensitive: (2) without damaging the physical integrity of the catalyst sample, e.g. no crushing or powdering of the sample: (3) allowing the exact position of the sample in the process vessel to be known: (4) allowing repeated sampling of the catalyst in the process vessel as the catalyst ages without affecting the integrity of the process vessel or the catalyst bed in the vessel: and (5) allowing return of the process vessel to service without leakage or contamination of the catalyst or process stream.

SUMMARY OF THE INVENTION

One aspect of the present invention is directed to a horizontal sample valve assembly for removing a sample from a bed of solid granular material contained in a vessel including a sampling passage in said vessel; a sampling valve mounted to said sampling passage: an extractor tube of a predetermined length adjacent to the sampling valve, the extraction tube positioned within the bed of solid granular material: and a means for extracting a sample of the solid granular material through said extractor tube and said sampling valve.

Another aspect of the present invention is a sample valve procedure for enabling removal of granular solid samples from vessels using the above sample valve assembly.

The present invention advantageously provides sampling solid catalysts from a process vessel such as, for example, a reactor vessel: (1) without changing the oxidation state of the catalyst sample, e.g. for catalysts that are air or moisture sensitive; (2) without damaging the physical integrity of the catalyst sample, e.g. no crushing or powdering of the sample: (3) allowing the exact position of the sample in the reactor to be known: (4) allowing repeated sampling of the catalyst in the reactor as it ages without affecting the integrity of the reactor or catalyst bed: and (5) allowing return of the reactor to service without leakage from the reactor or contamination of the catalyst or process stream inside the reactor.

DETAILED DESCRIPTION OF THE PREFERRED EMBODIMENT(S)

Figure 1:
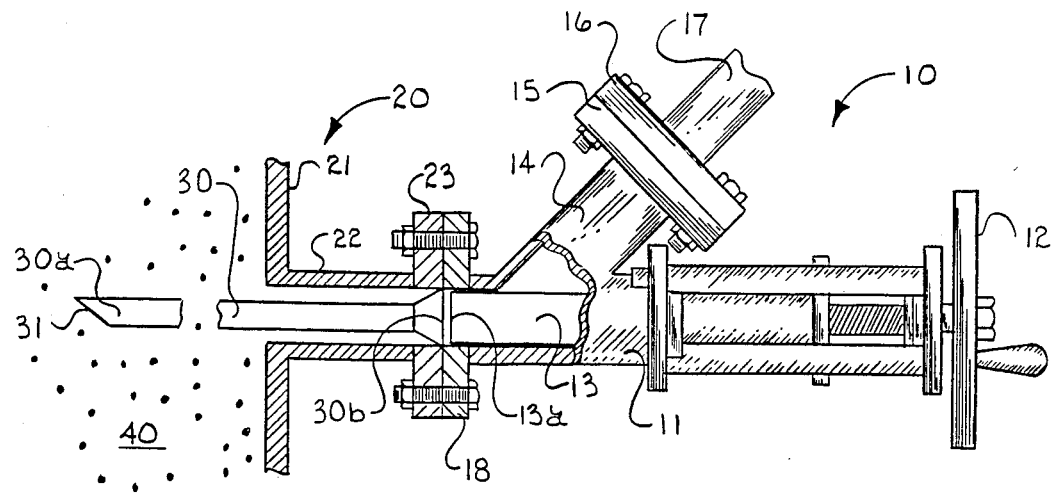
FIG. 1 is a partly cross-sectional, partly broken away, view showing a sampling valve assembly of the present invention.

With reference to FIG. 1, there is shown a sample valve assembly of the present invention including a sampling valve, generally designated as numeral 10, removeably mounted to a vessel, generally indicated as numeral 20; and an extraction tube (also interchangeably referred to herein as "extractor tube") or probe 30 positioned in a bed of solid granular material 40 contained in the vessel 20. Depending on the material being sampled, the vessel 20 used in conjunction with the present invention may include grain silos, rail cars, storage tanks, tank cars, reactor vessels, pipelines and the like. In this instance, the vessel 20 is a reactor vessel containing a catalyst material 40.

Herein, the present invention will be described with reference to sampling of a catalyst material 40. For example, catalyst users are able to use the valve and sampling method of the present invention for many, if not all, catalyst systems such as Dow Type KLP Catalyst, Dow Type K Catalyst and Dow Type P Catalyst commercially available from The Dow Chemical Company, or styrene catalyst, hydro-treater catalyst, and the like. A suitable catalyst material used in conjunction with the present invention is described in U.S. Pat. Nos. 4,440,956 and 4,483,206. It is contemplated, however, that the present invention may be used for removing a sample of granular solids of various particle sizes and shapes such as grain, phosphates, bisphenols, plastics and other bulk materials, particularly, those that require protection from the natural elements. The shapes of the solids include spherical, pellets, tablets, extrudates, powder, stars, and the like.

Preferably, the sampling valve 10 used in the present invention may be a conventional rod or plunger type valve which advances and retracts a shaft, rod or plunger to open and close the valve. Such valves, for example, may be manufactured by Fetterolf Corporation of Skippak, PA or Strahman Valves, Inc. of Florham Pk, NJ. Preferably, valves having a Y-shaped body similar to the valves described in U.S. Pat. No. 3,804,365 are used. U.S. Pat. No. 3,804,365 describes a similar plunger type valve used as a flush bottom tank valve for liquids.

In the present invention, the sampling valve 10 contains a Y-shaped body 11 horizontally aligned generally perpendicular to the side wall 21 of the vessel 20 with the bottom of the "Y" of the Y-shaped body 11 removably attached to a nozzle 22 via flange 23 on the vessel wall 21. In this instance, sampling valve 10 contains an actuating mechanism such as a motor drive or hand wheel 12 for horizontally moving a horizontally movable shaft or rod 13 to effect a seal of the valve on closing of the valve. In the closed position, the upper head 13a of the rod 13 is flush with the proximal end 30b (refer to FIG. 1) of a probe 30. The valve body 11 contains a branch 14 for discharging the sample collected and the branch 14 has a flange 15 which connects to the flange 16 of effluent piping 17, by convenient means such as nuts and bolts.

The sampling valve 10 has a radial flange 18 for securing, by convenient means such as nuts and bolts, to the vessel flange 23 which is welded or otherwise secured to a discharge nozzle 22, which in turn, is attached to the wall 21 of vessel 20.

The extension tube or probe 30 is welded or otherwise attached to the radial flange 18 of the sample valve 10 and extends into the vessel 20 through the nozzle orifice and beyond the inner wall of the vessel to a point wherein the distal end 30a of the probe 30 is inside the vessel. The probe 30 is of a catalyst-compatible material. The probe at its distal end 30a is preferably tapered. The proximal end 30b of the probe 30 is preferably attached flush with the flange orifice. The opening 31 at the tapered distal end 30a can be pointed in any direction, but is preferably installed inside the vessel with the opening 31 pointing down, such that the weight of catalyst, as it settles during use, would not force catalyst into the probe 30. Catalyst 40 thus entering the probe 30 (by force of the weight of the catalyst as it settles) would not be representative of catalyst in the reactor under process conditions and exposed to the full process flow.

The probe 30 is made of conventional tubular materials which are non-reactive or will not adversely affect the performance of the catalyst in the reactor vessel. Examples of materials used include metals such as aluminum, brass, stainless steel and the like. The schedule of the tubular metal should be sufficient to maintain the structural integrity of the probe under normal operating conditions of the reactor vessel. The diameter of the probe is not critical and may vary, but can be, for example, a ratio of 20:1 of the granular solid diameter.

In carrying out one process of the present invention, a sample valve 10 or a series of sample valves 10 are placed in or on a vessel 20 such as a reactor vessel, prior to the reactor being initially loaded with catalyst 40. The sample valves 10 should be positioned on the reactor 20 to allow removal of small portions of catalyst 40 from predetermined locations in the reactor, without affecting the catalyst sample or reactor catalyst bed integrity. The sample valves 10 are designed to enable closing before and after sampling without leakage, and contain a probe of a predetermined length and taper which determines where in the catalyst bed a sample is taken.

At the time of sampling the catalyst, the reactor 20 can be emptied of hydrocarbon and purged and padded with an inert gas such as nitrogen or methane, which is also used to purge the sample valve 10 and a sample receiving chamber, prior to the sample being taken through the sample valve.

Figure 3:
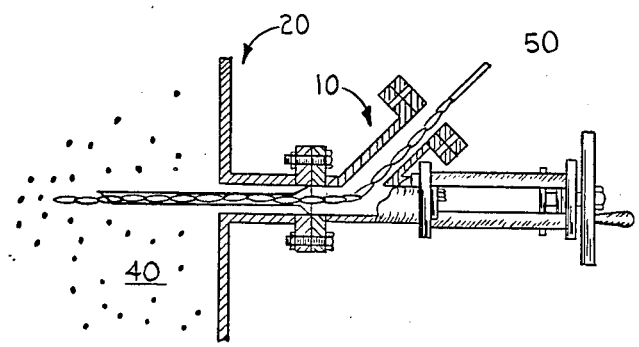
FIG. 3 is a partly cross-sectional, partly broken away view of one embodiment of the present invention.
Figure 4:
FIG. 4 is a perspective view of one type of auger means.

In one embodiment, with reference to FIG. 3 and 4, a sample of material 40 is extracted through the valve assembly of the present invention by a flexible auger 50 which is inserted through the sampling valve 10 through its branch passage 14 and probe 30. The auger 50 should be stiff enough so as not to break under normal operating conditions yet flexible enough to bend through the discharge orifices of the sampling valve 10. The auger material should not react with the catalyst or adversely affect the catalyst performance. Suitable materials for the auger can be of conventional materials such as aluminum, brass, stainless steel and the like.

Figure 5:
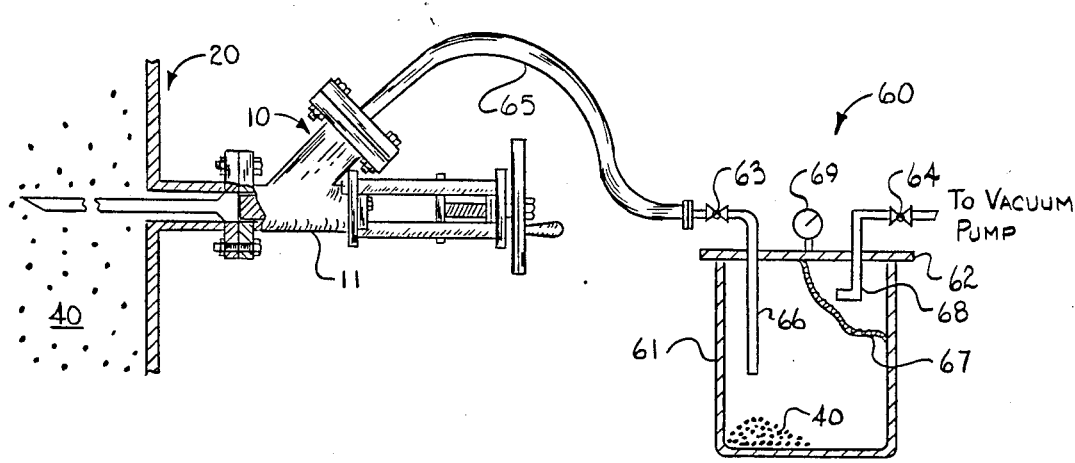
FIG. 5 is a schematic view of another embodiment of the present, invention.

In another embodiment, with reference to FIG. 5, especially useful for atmosphere-sensitive samples, a sample of material 40 is sucked by vacuum using a vacuum system, generally indicated by numeral 60, through the probe 30 and sample valve 10 into a collection pot 61, which could then be sealed using a cover 62 and block valves 63 and 64.

Depending on the type of catalyst and the specifics of its chemistry and the chemistry of the reactor process being sampled, the catalyst 40 can be removed from the reactor 20 by either the flexible auger 50 inserted through the sampling valve 10 into the catalyst bed 40 as shown in FIGS. 3 and 4, or by a vacuum suction system 60 which extracts the catalyst 40 through the sampling valve 10 into a collection/disengaging pot 61 as shown in FIG. 5.

For example, pelletized catalyst that is either large in size or not easily free flowing, or potentially wet or "sticky" due to the processing use, can be removed by means of a flexible auger 50 inserted through the valve 10 and probe 30 into the catalyst bed 40. Rotation of the auger 50 in one direction would pull the catalyst 40 through the probe 30 and sample valve 10 out of the reactor 20 and into a sample collection pot (not shown). The reactor 20, optionally, can be under an inert gas pad, or can be sampled under actual process conditions, if the collection system is designed to cope with the consequences of those conditions. Removal of the auger 50 from the sampling probe 30 would effectively remove essentially all of the catalyst sample 40 from the sample probe 30, effecting representative catalyst sampling immediately on subsequent sampling attempts.

Catalyst 40 that is more free flowing, due to small size, or that is more sensitive to exposure to atmospheric conditions, can be sucked from the reactor 20, through the probe 30 and sampling valve 10, by vacuum through a conduit 65, block valve 63 and inlet tube 66 and collected in the combination knock-out/vacuum disengaging pot 61. A filter 67 prevents the sample 40 from exiting with the vacuum stream through suction tube 68 and block valve 64. The vacuum in the pot 61 can be monitored with a vacuum gauge 69.

The pot 61 allows the catalyst sample 40 to drop from the vacuum stream and then to be isolated from the sampling system for removal to an analytical lab for testing. The reactor 20 should have an atmosphere consistent or compatible with that necessary to maintain the catalyst in a state the same as that of normal processing conditions, (for example, a nitrogen pad or other inert gas), under such processing conditions (for example, temperature, pressure and volatility) such that the catalyst sample, when taken, would not overwhelm or overload the vacuum removal system due to the presence or generation of large volumes of gas, vapor or liquid.

Once the sampling is complete, the sampling valve 10 is closed (in the case of the auger removal system, after the auger is removed from the valve), pushing any sample 40 not collected, but still in the valve 10 and/or probe 30, back into the probe 30. Since the probe 30 cannot be 100% full of catalyst due to the tapered end that ensures that catalyst 40 cannot enter the probe 30 until drawn in, the rod 13 of the valve 10 as it is closed pushes the excess catalyst 40 back into the probe 30. (This catalyst would not be representative on subsequent sampling attempts and would need to be discarded.) The valve 10, due to its design, seals on the periphery of the rod 13, not on the rod face or upper head surface 13a of the rod 13. The rod 13, as it is moved into the closed position, effectively cleans the sealing surface, and no catalyst "fines" are allowed to collect at the sealing surface. Valves of the prior art, which seal on a tapered surface of the rod face, collect catalyst "fines" or even catalyst pellets, and do not form an effective seal.

The additional pieces of the sampling system could be removed from the port on the valve assembly and the port closed off, valved shut, blinded or covered to further ensure against leaks either out of or into the reactor and to wait until subsequent sampling.

When sampling is completed, the auger 50 or vacuum system 60 is stopped, the sample valve 10 is closed to seal off the sample port or branch 14 and the equipment is removed. The process of the present invention insures that both the catalyst sample 40 and reactor 20 contents are not contaminated by exposure to the atmosphere.

Figure 2:
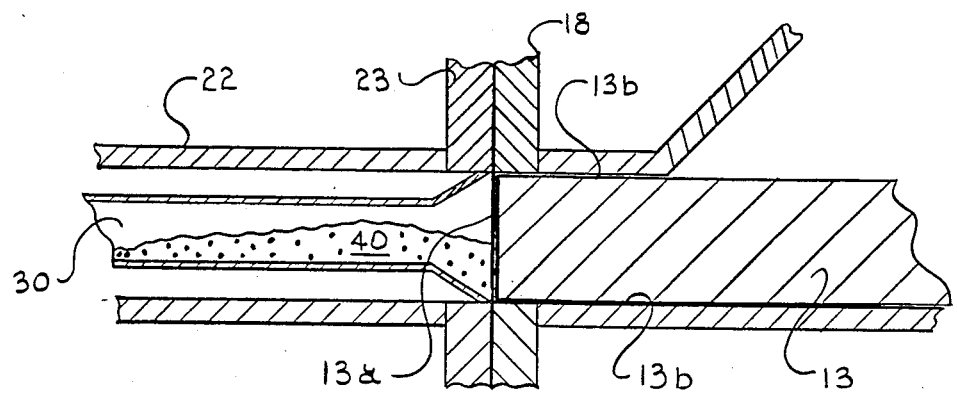
FIG. 2 is an enlarged cross-sectional view of the sealing area of FIG. 1.

Upon closure of the sampling valve 10 (FIG. 2), the rod 13 of sampling valve 10 pushes any sample 40 left in the valve back into the probe 30 and seals on the sides 13b of the rod 13, not on the face of the rod 13a. This point is very important and critical to the effectiveness of the present invention. A valve of the prior art which seals on its face—the front end of the rod extending toward the sample location—has the disadvantage that catalyst pellets and/or catalyst fragments or "fines" can become trapped between the two mating surfaces of the valve, effectively prohibiting the two surfaces to mate, preventing a seal and causing the valve to leak at its sealing surface. Additional force exerted to close the seal will likely result in permanent damage to the mating surface. The valve 10 of the present invention seals on the side 13b of the rod 13 and does not have the problems of the prior art valve, because the face 13a of the rod 13 of the valve 10 effectively sweeps the catalyst particles away from the mating surfaces as the valve is closed.

The probe 30 will not be completely full of catalyst sample due to the auger or vacuum means of removing the sample. During the next sampling time, the first volume of sample is discarded as not representative of that in the reactor.

As the catalyst bed 40 settles in the reactor as a result of use, the extension probe 30 on the valve 10 would likely be bent. Depending upon the severity of the bend in the probe 30, it may still be possible to extract catalyst samples through the probe. The tip of the probe would be expected to settle at essentially the same rate as the catalyst in the bed, enabling sampling of catalyst from the same relative area in the bed as initially intended. If the probe is too severely bent, it could be replaced with a new probe on the same valve during catalyst change-out.

Figure 6:
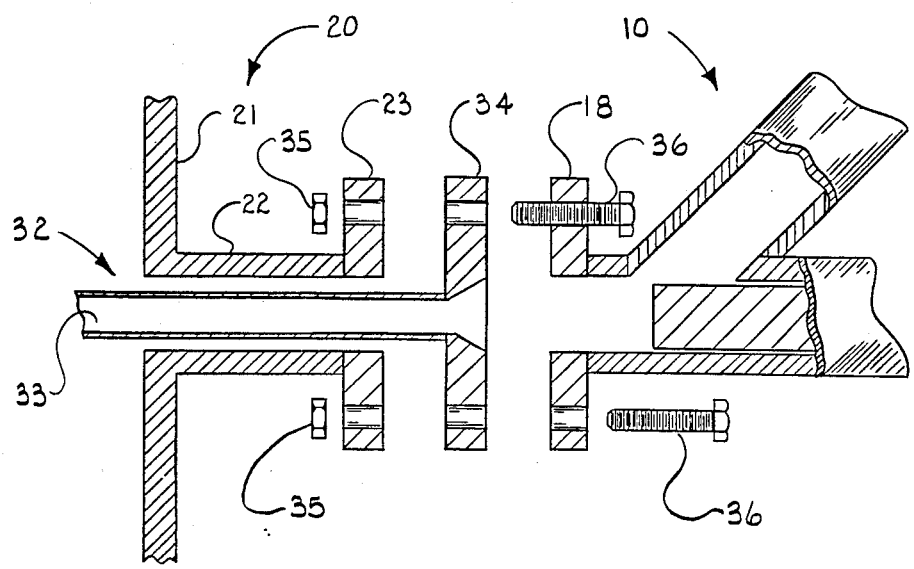
FIG. 6 is another embodiment of the sample valve assembly of the present invention.

In FIG. 6, there is shown a removable probe, generally indicated as numberal 32 which is readily replaced when it becomes bent. The probe 32 comprises a probe tube 33 welded or otherwise attached to a flange 34 which can be mounted to the nozzle 21 of the vessel 20 by sandwiching the flange 34 between the flange 23 of the nozzle and flange 18 of the sample valve 10 by convenient means such as nuts 35 and bolts 36.

The advantage of the present invention is that the sampling valve 10 for the catalyst sample is initially an integral part of the reactor prior to the initial filling with catalyst. The probe 30 of the valve assembly of the present invention, extending into the reactor through a nozzle at the reactor wall, determines where the sample will be taken with no uncertainty. Multiple sampling assemblies mounted on a reactor, especially on a developmental pilot scale or commercial scale reactor, enable a full complement of representative catalyst samples to be taken without affecting catalyst or reactor integrity, minimizing downtime, expense, and exposure of the sampling personnel. Probes can be of varying length to allow sampling at the core or wall of the reactor or anywhere in-between. By using an auger or vacuum to cause the catalyst to enter the probe, fresh, representative catalyst samples are insured. The small volume of catalyst left in the probe from one sampling session to the next can be discarded when a subsequent sample is taken.

The sampling technique allows sampling solids in a fixed bed, that is, sampling solid catalyst in a packed vessel. The invention could also be used for sampling fluidized catalyst in a fluidized bed. The unique combination of parts and application of these parts to sample a solid, be it a fixed or fluidized bed situation versus sampling liquids or slurries, and the technique used for the application, are novel.

What is claimed is:

1. A horizontal sample valve assembly for removing a sample from a bed of solid granular material contained in a vessel comprising:
   a. a sampling passage in said vessel having means for mounting thereon a sampling valve;
   b. the sampling valve mounted to said sampling passage, said sampling valve having a horizontally disposed body which houses therein, a horizontally disposed valve shaft which is in operable attachment to a drive means at its outward end, with its inward end operable for sealing the valve shaft against a valve seat when the valve is in the closed position against the sampling passage;

said valve assembly also having an effluent conduit member branched from the valve body and which communicates with the interior of the valve body near the valve seat when the valve shaft is in the open position;
   c. an extractor tube of a predetermined length to having an end at the valve seat of the sampling valve shaft, and a distal end positioned within the bed of solid granular material; and
   d. a means for extracting a sample of the solid granular material through said extractor tube, said effluent conduit member, and said sampling valve.

2. The sample valve assembly of claim 1 wherein the extractor means is a flexible auger inserted through said effluent conduit member and said extractor tube.

3. The sample valve assembly of claim 1 wherein the extractor means is a vacuum suction means connected through said effluent conduit member and to said extractor tube.

4. The sample valve assembly of claim 1 wherein the extractor tube at its distal end, which is within the granular material, is adapted for extracting a sample from a predetermined location of the bed of material.

5. The sample valve assembly of claim 1 wherein the vessel is sealed from the atmosphere.

6. The sample valve assembly of claim 1 wherein the solid granular material is catalyst.

7. The sample valve assembly of claim 1 wherein the extractor tube is removably mounted to said vessel.

8. The sample valve assembly of claim 1 wherein the sampling valve is a plunger type valve.

9. The sample valve assembly of claim 1 wherein the vessel is a reactor vessel.

10. A process for removing a sample of solid granular material from a vessel containing a bed of solid granular material comprising extracting a sample of the slid granular material, without exposing the material to the atmosphere, through an extractor tube positioned a predetermined distance within the bed of solid granular material and a horizontally disposed sampling valve, said valve having an effluent conduit member branched outwardly from the interior thereof, said valve being mounted to a sampling passage in said vessel.

* * * * *

UNITED STATES PATENT AND TRADEMARK OFFICE
CERTIFICATE OF CORRECTION

PATENT NO. : 4,958,527

DATED : September 25, 1990

INVENTOR(S) : Mark C. Couvillion

It is certified that error appears in the above-identified patent and that said Letters Patent is hereby corrected as shown below:

Col. 1, line 23 "the sample:" should read --the sample;--.

Col. 1, line 24, "the sample:" should read --the sample;--.

Col. 1, line 25, "of the catalysts:" should read --of the catalyst;--.

Col. 1, line 26, "of the reactor:" should read --of the reactor;--.

Col. 1, line 27, "cant down time: should read --can't down time;

Col. 1, line 58, "bed by force:" should read --bed by force;--.

Col. 1, line 60, "a sample:" should read --a sample;--.

Col. 2, line 33, "moisture sensitive:" should read --moisture sensitive;--.

Col. 2, line 35, "of the sample:" should read --of the sample;--.

Col. 2, line 37, "to be known:" should read --to be known;--.

Col. 2, line 40, "in the vessel:" should read --in the vessel;--.

Col. 2, line 49, "sampling passage:" should read --sampling passage;--.

Col. 2, line 52, "granular material:" should read --granular material;--.

Col. 2, line 65, "of the sample:" should read --of the sample;--.

Col. 2, line 66, "to be known:" should read --to be known;--.

Col. 3, line 17, "the present, invention." should read --the present invention.--.

UNITED STATES PATENT AND TRADEMARK OFFICE
CERTIFICATE OF CORRECTION

PATENT NO. : 4,958,527
DATED : September 27, 1990
INVENTOR(S) : Mark C. Couvillion It is certified that error appears in the above-identified patent and that said Letters Patent is hereby corrected as shown below:

Col. 8, line 6, "length to" should read --length--.

Col. 8, line 36, "of the slid granular" should read --of the solid granular--.

Signed and Sealed this

Twenty-first Day of July, 1992

Attest:

DOUGLAS B. COMER

Attesting Officer

Acting Commissioner of Patents and Trademarks